US012667444B2

(12) United States Patent
Oeler et al.

(10) Patent No.: US 12,667,444 B2
(45) Date of Patent: Jun. 30, 2026

(54) PACKAGING ARRANGEMENT FOR A MEDICAL DEVICE

(71) Applicant: BIOTRONIK AG, Bülach (CH)

(72) Inventors: Moritz Oeler, Zurich (CH); Johannes Schampel, Birmensdorf (CH); Bram Hermans, Venray (NL)

(73) Assignee: BIOTRONIK AG, Buelach (CH)

( * ) Notice: Subject to any disclaimer, the term of this patent is extended or adjusted under 35 U.S.C. 154(b) by 11 days.

(21) Appl. No.: 18/833,142

(22) PCT Filed: Jan. 13, 2023

(86) PCT No.: PCT/EP2023/050697

§ 371 (c)(1),
(2) Date: Jul. 25, 2024

(87) PCT Pub. No.: WO2023/156092

PCT Pub. Date: Aug. 24, 2023

(65) Prior Publication Data

US 2025/0160989 A1     May 22, 2025

(30) Foreign Application Priority Data

Feb. 15, 2022     (EP) ..................................... 22156698

(51) Int. Cl.
*A61B 50/33*     (2016.01)
*A61B 50/30*     (2016.01)
(52) U.S. Cl.
CPC ...... *A61B 50/33* (2016.02); *A61B 2050/3008* (2016.02)
(58) Field of Classification Search
CPC .. A61B 50/33; A61B 50/30; A61B 2050/3008

USPC .......................................................... 206/363
See application file for complete search history.

(56) References Cited

U.S. PATENT DOCUMENTS

| | | | | |
|---|---|---|---|---|
| 4,216,860 A | * | 8/1980 | Heimann | A61M 25/002 |
| | | | | 206/370 |
| 5,947,284 A | * | 9/1999 | Foster | A61B 50/30 |
| | | | | 206/364 |
| 9,265,578 B2 | * | 2/2016 | Dacey | A61B 50/33 |
| 2012/0103840 A1 | * | 5/2012 | McCaffrey | A61M 25/002 |
| | | | | 29/428 |
| 2015/0196391 A1 | * | 7/2015 | Dwork | A61F 2/2427 |
| | | | | 53/440 |

(Continued)

OTHER PUBLICATIONS

International Search Report from the corresponding International Patent Application No. PCT/EP2023/050697, dated Mar. 13, 2023.

*Primary Examiner* — Steven A. Reynolds
(74) *Attorney, Agent, or Firm* — Greer, Burns & Crain, Ltd.; Steven P. Fallon

(57) ABSTRACT

A packaging arrangement for a medical device includes at least one device recess configured to receive the medical device. A loading is basin configured to receive a liquid that can manipulate the medical device housed in the at least one device recess or to be connected to the medical device housed in the at least one device recess. A spillway basin is connected to the loading basin via a spillway passage having a spillway passage inflow and a spillway passage outflow. The spillway passage includes a downward slope from the spillway passage inflow to the spillway passage outflow configured to promote a liquid flow to the spillway passage outflow.

12 Claims, 2 Drawing Sheets

(56)        References Cited

U.S. PATENT DOCUMENTS

| 2016/0213441 | A1* | 7/2016 | Connolly | ............... | B65D 45/20 |
| 2016/0228676 | A1* | 8/2016 | Glithero | ............ | A61M 25/0017 |
| 2017/0056149 | A1* | 3/2017 | Rajpara | ................ | A61F 2/9525 |
| 2019/0358018 | A1 | 11/2019 | Rajpara et al. | | |
| 2020/0360103 | A1* | 11/2020 | Knapp | ................... | A61B 50/33 |
| 2021/0369379 | A1 | 12/2021 | Bandyopadhyay et al. | | |

* cited by examiner

PACKAGING ARRANGEMENT FOR A MEDICAL DEVICE

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2023/050697, which was filed Jan. 13, 2023, which application claimed priority from EP application Ser. No. 22/156,698.7, which was filed Feb. 15, 2022.

FIELD OF THE INVENTION

A field of the invention concerns packaging arrangements for a medical device.

BACKGROUND

US 2012/0305441 A1 discloses a packaging for a delivering catheter system. Thereby, the packaging comprises two packaging parts that are connected to each other with a hinge. This hinge enables a relative movement between the two packaging parts; however, it keeps those packaging parts always closely together.

One-part packages are known that are also intended for housing a medical device. Such packages may comprise a recess to be used as a container for a liquid. Such liquid may be a rinsing liquid, a loading liquid, a physiologically acceptable liquid or the like having a technical function for packaging and/or preparation purposes of the medical device.

When the packaging is opened, liquid is filled into the recess. Then, the medical device or an additional medical device to be manipulated by the packed medical device is rinsed in the rinsing liquid. If, e.g., a prosthetic heart valve is to be delivered to a patient, the packaging of a delivery catheter contains such a recess which is filled with a rinsing liquid prior to implanting the prosthetic heart valve. Then, the prosthetic heart valve is submerged in the liquid and thoroughly rinsed prior to its implantation. The volume space occupied by the prosthetic heart valve, the user's hands and further components required for the rinsing procedure serve for displacement of rinsing liquid from the recess. This displacement typically leads to an overflow or spillage of rinsing liquid out of the packaging. The respective site of operation needs to be cleaned afterwards.

To avoid such spillage, e.g. of rinsing liquid, packages have been developed in prior art that contain a bigger recess so as to provide a bigger volume space for a liquid. This, however, enlarges the required overall space of the packaging. This, in turn, is disadvantageous with respect to storage and transport capacities and the general handling of such a packaging.

SUMMARY OF THE INVENTION

A preferred packaging arrangement for a medical device includes at least one device recess configured to receive the medical device. A loading is basin configured to receive a liquid that can manipulate the medical device housed in the at least one device recess or can be connected to the medical device housed in the at least one device recess. A spillway basin is connected to the loading basin via a spillway passage having a spillway passage inflow and a spillway passage outflow. The spillway passage includes a downward slope from the spillway passage inflow to the spillway passage outflow configured to promote a liquid flow to the spillway passage outflow.

BRIEF DESCRIPTION OF THE DRAWINGS

Further details of aspects of the present invention will be explained with respect to exemplary embodiments and accompanying Figures. In the Figures.

DETAILED DESCRIPTION OF THE PREFERRED EMBODIMENTS

Figure 1:
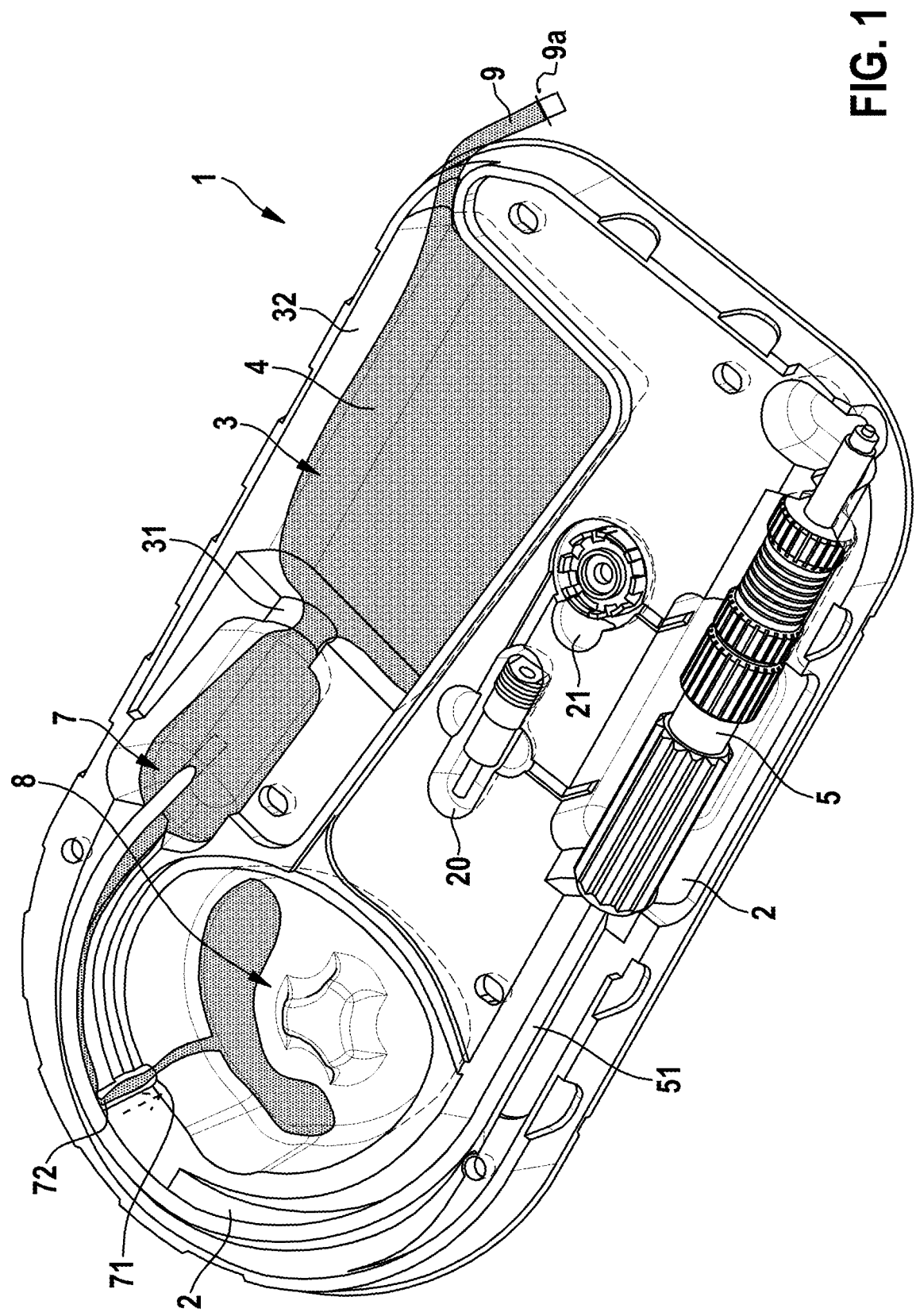
FIG. 1 shows a perspective view of an embodiment of a packaging arrangement for a medical device.

A preferred packaging for a medical device overcomes the described spillage problems of prior art packaging but nonetheless does not have a bigger volume than prior art packages for the above-mentioned liquids.

A packaging arrangement is configured to house a medical device. The packaging arrangement comprises at least one device recess for receiving a medical device. It further comprises a loading basin intended to receive a liquid for manipulating the medical device housed in the at least one device recess. Alternatively, the liquid that is to be filled into the loading basin can also be used for manipulating a medical device that is intended to be connected to medical device housed in the at least one device recess.

According to an aspect of the present invention, the packaging arrangement further comprises a spillway basin. In this context, the loading basin is connected to the spillway basin by a spillway passage. This spillway passage has a spillway passage inflow and a spillway passage outflow. The spillway passage inflow is oriented towards and is in fluid communication with the loading basin. The spillway passage outflow is oriented towards and is in fluid communication with the spillway basin. In one embodiment, the spillway passage exhibits a downward slope from the spillway passage inflow to the spillway passage outflow. Thus, essential is that the spillway passage in a suitable configuration comprises a point of highest level defining the actual liquid level within the loading basin. Thus, liquid entering the spillway passage from the loading basin through the spillway passage inflow can flow downwards the spillway passage to the spillway passage outflow and can enter the spillway passage outflow towards the spillway basin. The spillway basin thus serves for accommodating excess rinsing liquid that has been filled into the loading basin during a loading procedure of the medical device contained in the packaging arrangement or during other preparatory work during which a rinsing liquid is required and filled into the loading basin of the packaging arrangement.

Expressed in other words, the spillway basin serves as receptacle for any liquid that is displaced from the loading basin by a medical device (such as a catheter and/or a prosthesis), the user's hands and further components required for the procedure, wherein the procedure typically is a manipulating procedure of the medical device. By providing such spillway basin, controlled drainage of liquid from the loading basin is achieved so that the liquid does not spill over the side walls of the loading basin to the surrounding of the packaging arrangement.

As a result, an optimal liquid level can be maintained in the loading basin. At the same time, an optimized use of material and space necessary for the packaging arrangement is achieved resulting in an optimized loading basin height. An optimized loading basin height, in turn, is desirable as it defines the total size of the packaging arrangement. Thus, the provision of the spillway basin connected via the spillway passage to the loading basin enables a thinner design of the packaging arrangement so that the required space of the packaging arrangement is reduced with respect to prior art solutions. At the same time, the risk of liquid spillage is significantly reduced or even completely avoided by the provision of an overflow or drainage feature in the nature of the spillway passage and the spillway basin in fluid communication with the loading basin.

The principle of overflow protection applied by the packaging arrangement according to an aspect of the present invention can generally be applied to any tray packaging solutions which require liquid management. It is particularly appropriate for a medical device packaging. In this context, the packaging arrangement can be designed as one-tray packaging or as two-tray packaging or as multi-tray packaging.

In an embodiment, the spillway passage inflow is located at a higher relative height than the spillway passage outflow. Then, a downward slope of the spillway passage is implemented in a particularly easy way.

The term "relative height" used throughout the present description relates to the height of individual components of the packaging arrangement when the packaging arrangement is present in its intended orientation of use. Then, a component having a higher relative height is located above a component having a lower relative height. A bottom region of the packaging arrangement has the lowest relative height. A top region of the packaging arrangement has the highest relative height.

In an embodiment, the medical device to be contained by the packaging arrangement is a catheter, in particular a delivery catheter for an implant, in particular a delivery catheter for delivering an implant to an implantation site through a blood vessel of a patient. In an embodiment, the implant is a heart valve prosthesis, e.g., an aortic valve prosthesis. In an embodiment, the delivery catheter is intended to be used in transcatheter aortic valve implantation (TAVI) or transcatheter aortic valve replacement (TAVR) applications as well as, e.g., for medical occluding means such as LAAC or for an aortic graft, but not limited thereto.

In an embodiment, the spillway passage comprises a spillway barrier. This spillway barrier is arranged between the spillway passage inflow and the spillway passage outflow. This spillway barrier is designed such that a liquid flowing from the spillway passage inflow through the spillway passage to the spillway passage outflow needs to flow over the spillway barrier. Depending on the relative height of the spillway barrier, the flow of liquid through the spillway passage can be adjusted. Thus, the spillway barrier acts like a weir.

In an embodiment, a top of the spillway barrier is located at a higher relative height than the spillway passage inflow. In this embodiment, a liquid originating from the loading basin needs to overcome the spillway barrier in order to reach the spillway basin. Thereby, the height of the top of the spillway basin can be chosen such that the liquid only flows over the top of the spillway barrier once it has reached its optimum filling level in the loading basin.

In an embodiment, the spillway barrier is movable with respect to the spillway passage. Such movability of the spillway barrier enables an adjustment of the relative height of the top of the spillway barrier. Then, it is particularly easy to adjust the height of the top of the spillway barrier to the actual needs to achieve an optimum filling level of the loading basin with a liquid. In this embodiment, the spillway barrier acts like an adjustable weir. It is possible to implement this embodiment by a spillway barrier that is movable in its entirety. It is further possible to implement this embodiment by a spillway barrier that comprises a movable part that can be extended or retracted with respect to a stationary part of the spillway barrier.

In an embodiment, a bottom of the spillway basin is located at a relative height not being lower than a relative height of the loading basin. Thus, the bottom of the spillway basin is, in this embodiment, arranged at an equal relative height like a bottom of the loading basin or, alternatively, at a higher relative height than the bottom of the loading basin. In doing so, the overall height or thickness of the packaging arrangement is not increased by the provision of the spillway basin. Since the spillway basin is typically arranged in an area of the packaging arrangement which is necessarily present in the packaging arrangement anyway, the provision of the spillway basin does not increase the overall dimensions of the packaging arrangement.

In an embodiment, the loading basin, the spillway passage and/or the spillway basin comprises a sidewall. In this context, a rim is provided in the sidewall between a top of the sidewall and a bottom of the sidewall. This rim provides an additional volume for liquid being present in the compartment that is confined by the sidewall (i.e., the loading basin, the spillway passage and/or the spillway basin). Thus, the additional rim provides an additional spillway volume and further reduces the risk of an undesired spillage of any liquid contained in the loading basin, the spillway passage and/or the spillway basin. The rim can be manufactured upon manufacturing the whole packaging arrangement, e.g., by embossing it during a thermoforming process, in particular in an embodiment in which the packaging arrangement is produced as thermoformed blister packaging.

In an embodiment, the packaging arrangement comprises a discharging element. This discharging element is in fluid communication with an interior of the loading basin and serves for discharging liquid being contained in the loading basin. Thus, the discharging element facilitates an emptying of the loading basin and provides a second regular possibility for a liquid contained in the loading basin to leave the loading basin (besides the first possibility of flowing through the spillway passage towards the spillway basin).

In an embodiment, the discharging element comprises a discharging element inflow oriented to the interior of the loading basin. In a first variant, the discharging element is located at a relative height corresponding to a relative height between an optimum filling level of the loading basin and a top of a sidewall of the loading basin. Then, a liquid contained in the loading basin cannot only leave the loading basin through the spillway passage inflow towards the spillway passage and the spillway basin, but also through the discharging element to be discharged from the packaging arrangement.

In a second alternative of this embodiment, the relative height of the discharging element corresponds to a relative height between the spillway passage inflow and a top of a sidewall of the loading basin. In this alternative, any liquid contained in the loading basin can only flow through the discharging element in case that a discharge via the spillway passage inflow and the spillway passage is obstructed or cannot be achieved in sufficiently short time. If, however, the spillway passage works as intended, the liquid contained in the loading basin typically exits the loading basin through the spillway passage inflow and the spillway passage and then reaches the spillway basin through the spillway passage outflow.

In a third alternative of this embodiment, the relative height of the discharging element corresponds to a relative height between a top of the spillway barrier and a top of a sidewall of the spillway passage. In this context, the spillway barrier is—as already defined above—located between the spillway passage inflow and the spillway passage outflow. The spillway barrier is an element that needs to be overcome by liquid flowing from the spillway passage inflow through the spillway passage in order to reach the spillway passage outflow. In this variant, the discharging element serves as additional security discharging element through which liquid contained in the loading basin can flow if the liquid level in the loading basin and the spillway passage rises above the relative height of the top of the spillway barrier. Since the discharging element is, in this variant of the presently discussed embodiment, arranged below a relative height of the top of the sidewall of the spillway passage, liquid contained in the loading basin will first enter the discharging element prior to spilling above the sidewall of the spillway passage. Thus, also in this embodiment, the additional discharging element serves as security discharge for excess liquid being present in the loading basin and the spillway passage.

In an embodiment, the discharging element comprises a valve element. This valve element serves for opening or closing a fluid passage within the discharging element.

If the valve element is closed, no fluid will be able to leave the loading basin through the discharging element. If the valve element is opened, liquid contained in the loading basin can be discharged through the discharging element if the filling level of the liquid is sufficiently high so that the liquid can enter the discharging element or if the packaging arrangement is tilted so as to pour the liquid through the discharging element out of the loading basin. The valve element can be implemented, e.g., as a tap or as a removable blocking element like a plug.

In an embodiment, the discharging element is arranged at a corner of the packaging arrangement. In particular, it is at the same time arranged at the corner of the loading basin. Then, it is particularly easy to drain any liquid contained in the loading basin through the discharging element.

In an embodiment, the spillway basin serves for accommodating a removable rinsing tray in a storage or transport state of the packaging arrangement. Since packaging arrangements typically contain rinsing containers, this embodiment utilizes space that needs to be provided for in any case for a second function, namely as spillway basin. The rinsing tray typically comprises a plurality of recesses, wherein each of these recesses serves for receiving a rinsing liquid once the packaging arrangement has been opened and a preparation of a medical device contained in the packaging arrangement is to be started. Such state of the packaging arrangement can also be denoted as preparation state. Then, the rinsing tray is removed from the packaging tray, leaving a free recess in the packaging arrangement. This free recess will then serve as spillway basin, whereas the removed rinsing tray is placed besides the packaging arrangement or connected to an outside of the packaging arrangement.

In an embodiment, the device recess is configured to receive an oblong medical device in a curved position. Examples for appropriate oblong medical devices are given above. A particular appropriate example is a TAVI/TAVR delivery catheter, wherein the catheter handle would be contained in the packaging arrangement in its given shape and a catheter shaft would be contained in the packaging arrangement in a curved position.

In an embodiment, the device recess is configured to receive a TAVI/TAVR delivery catheter.

All embodiments as disclosed herein can be combined in any desired way.

FIG. 1 shows a TAVI/TAVR delivery catheter packaging 1 that serves as packaging arrangement for a medical device. The TAVI/TAVR delivery catheter packaging 1 comprises a TAVI/TAVR catheter recess 2 that serves as device recesses. Within this TAVI/TAVR delivery catheter recess 2, a TAVI/TAVR delivery catheter 5 is housed. A catheter shaft 51 of the TAVI/TAVR delivery catheter 5 is held in a curved position within the TAVI/TAVR delivery catheter recess 2.

The TAVI/TAVR delivery catheter packaging 1 further comprises additional device recesses 20, 21 that serve for housing additional medical devices to be used in connection with the TAVI/TAVR delivery catheter 5.

The TAVI/TAVR delivery catheter packaging 1 further comprises a loading basin 3 that is kept in a dry state as long as the TAVI/TAVR delivery catheter packaging 1 is stored or transported (i.e., as long as it is kept in its storage state). However, upon starting a TAVI/TAVR procedure, the TAVI/TAVR delivery catheter packaging 1 is opened and a liquid 4 is filled into the loading basin 3. The liquid serves for rinsing and/or loading an aortic valve implant that is to be implanted with the help of the TAVI/TAVR delivery catheter 5; e.g., loading to a suitable catheter device 5 for delivery of said implant. When the aortic valve implant is rinsed in the loading basin and afterwards loaded into a loading portion of the TAVI/TAVR delivery catheter 5, the liquid level of the rinsing liquid 4 can rise in the loading basin 3. In order to avoid spillage of the rinsing liquid 4, the loading basin 3 comprises an outflow opening 31 that serves as spillway passage inflow. The outflow opening 31 fluidly connects the loading basin 3 with a spillway passage 7 having a spillway passage outflow 71 at its second end being remotely arranged from its first end at the outflow opening 31 of the loading basin 3.

If the rinsing liquid 4 flows from the loading basin 3 through the outflow opening 31 of the loading basin 3 to the spillway passage 7 and through the spillway passage 7 to the spillway passage outflow 71, it enters a spillway basin 8. Thus, the rinsing liquid 4 is not spilled over a sidewall 32 of the loading basin 3 even in case of an increased filling level of the loading basin 3, but rather can flow into the spillway basin 8.

A bottom of the spillway basin 8 is not deeper than a bottom of the loading basin 3 so that the spillway basin 8 will not increase an overall height of the TAVI/TAVR delivery catheter packaging 1.

In order to be able to discharge the rinsing liquid 4 from the loading basin 3 not only towards the spillway basin 8, the TAVI/TAVR delivery catheter packaging 1 comprises a spout 9 that is arranged at a corner of the TAVI/TAVR delivery catheter packaging 1 and at the same time at a corner of the loading basin 3. This spout 9 serves as discharging element and ensures spillage-free discharge of rinsing liquid 4 from the loading basin 3 if the loading basin 3 is to be emptied. For this purpose, the spout 9 is equipped with a tap by which it can be closed and opened as desired.

To provide an emergency overflow appliance, the tap of the spout 9 can be kept open during manipulating a medical device within the rinsing liquid 4 in the loading basin 3. Since the spout 9 is arranged in a relative height of the TAVI/TAVR delivery catheter packaging 1 that is higher than the height of the outflow opening 31 of the loading basin 3, typically no rinsing liquid 4 will enter into the spout 9. Upon a rise of the filling level of the rinsing liquid 4, the rinsing liquid 4 contained in the loading basin 3 will first enter the spillway passage 7 through the outflow opening 31 of the loading basin 3 and will discharged through the spout 9 only in case of a significant increase of its filling level.

The spillway passage 7 further comprises a spillway barrier 72 over which the rinsing liquid 4 needs to flow in order to reach the spillway passage outflow 71 and finally the spillway basin 8. This spillway barrier 72 can define the highest point of the spillway passage 7 and thus defines the overall flowing characteristics of the rinsing liquid 4 flowing through the spillway passage 7.

Even in case that a top of the spillway barrier 72 is arranged at a higher relative height than the lowest point of the outflow opening 31 of the loading basin 3, the spillway passage has a downward slope (though not a continuous downward slope) from the outflow opening 31 of the loading basin 3 towards the spillway outflow 71.

Figure 2:
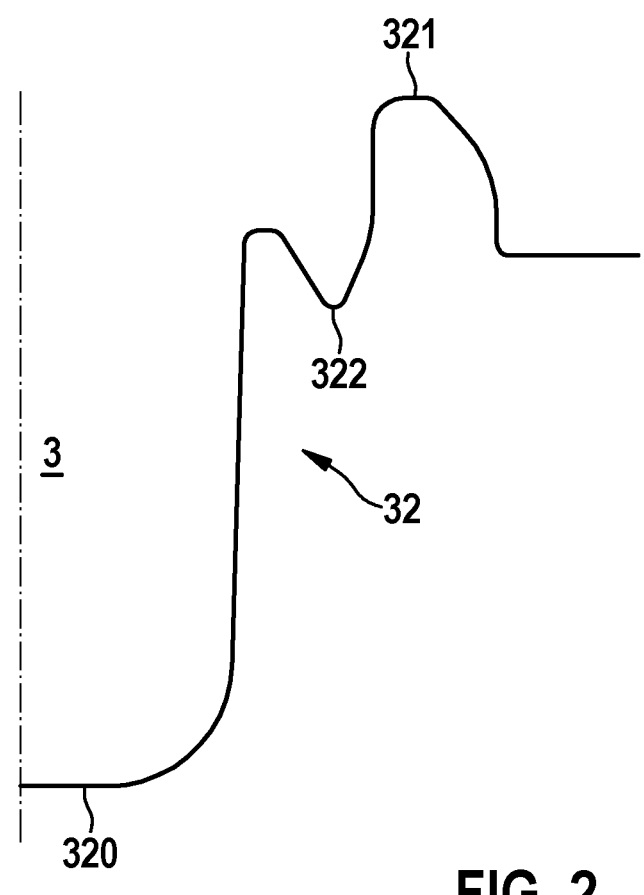
FIG. 2 shows a schematic cross-sectional view of a sidewall of a loading basin of a packaging arrangement.

FIG. 2 shows a cross-sectional view of an embodiment of a sidewall 32 of a loading basin 3 of a TAVI/TAVR delivery catheter packaging 1. The same or similar elements will be referred to with the same numeral references as in FIG. 1 even though the embodiment of FIG. 1 is not equipped with features that will be explained in connection with FIG. 2.

The sidewall 32 shown in FIG. 2 has a bottom 320 and a top 321. Between the bottom 320 and the top 321 of the sidewall 32, a rim 322 is arranged that provides an additional volume for a liquid (like the rinsing liquid 4 depicted in FIG. 1) that is contained in the loading basin 3 being confined by the sidewall 32. Thus, the rim 322 can be considered as safety zone to additionally reduce the risk of liquid spillage out of the loading basin 3.

Consequently, the rim 322 is an additional anti-spillage element that enhances the overall anti-spillage properties of the TAVI/TAVR delivery catheter packaging 1 in combination with the spillway passage 7 and the spillway basin 71 (cf. FIG. 1). Said rim 322 may further comprise some sort of an outflow back towards the loading and/or rinsing basin.

Features of preferred embodiments that includes features described above include a packaging arrangement for a medical device, the packaging arrangement (1) comprising at least one device recess (2, 20, 21) for receiving a medical device (5) and a loading basin (3) intended to receive a liquid (4) for manipulating a medical device (5) housed in the at least one device recess (2, 20, 21) or being intended to be connected to a medical device (5) housed in the at least one device recess (2, 20, 21). The packaging arrangement (1) further comprises a spillway basin (8), wherein the loading basin (3) is connected to the spillway basin (8) via a spillway passage (7) having a spillway passage inflow (31) and a spillway passage outflow (71), wherein the spillway passage (7) exhibits a downward slope from the spillway passage inflow (31) to the spillway passage outflow (71) such that a liquid flow is allowed.

The the spillway passage (7) preferably comprises a spillway barrier (72) between the spillway passage inflow (31) and the spillway passage outflow (71), wherein the spillway barrier (72) needs to be overcome by a liquid (4) flowing from the spillway passage inflow (31) through the spillway passage (7) in order to reach the spillway passage outflow (71).

A top of the spillway barrier (72) is preferably located at a higher relative height than the spillway passage inflow (31) and/or spillway passage outflow.

The spillway barrier is preferably movable with respect to the spillway passage (7) so as to allow an adjustment of a relative height of a top of the spillway barrier (72).

A bottom of the spillway basin (8) is preferably located at a relative height not being lower than a relative height of the loading basin (3).

At least one of the loading basin (3), the spillway passage (7) and the spillway basin (8) preferably comprises a sidewall (32) having a rim (322) between a top (321) of the sidewall (32) and a bottom (320) of the sidewall (32), the rim (322) providing an additional volume for a liquid (4) being present in a compartment chosen from the loading basin (3), the spillway passage (7) and the spillway basin (8) that is confined by the sidewall (32).

A discharging element can be in fluid communication with an interior of the loading basin (3), preferably the discharging element being a plug or a valve, preferably being placed at the bottom portion of the packaging arrangement.

The discharging element can include a discharging element inflow oriented to the interior of the loading basin (3) and located at a relative height that corresponds to at least one of a) a relative height between an optimum fill level of the loading basin (3) and a top of a sidewall (32) of the loading basin (3), b) a relative height between the spillway passage inflow (31) and a top of a sidewall (32) of the loading basin (3), and c) a relative height between a top of a spillway barrier (72) and a top of a sidewall of the spillway passage (7), wherein the spillway barrier (72) is located between the spillway passage inflow (31) and the spillway passage outflow (71) and needs to be overcome by a liquid (4) flowing from the spillway passage inflow (31) through the spillway passage (7) in order to reach the spillway passage outflow (71).

The discharging element (9) comprises a blocking element such as a valve or a removable plugging structure (9a) via which a fluid passage within the discharging element (9) can be opened or closed.

The discharging element (9) can be arranged at a corner of the packaging arrangement (1).

The spillway basin (8) or loading basin can serve for accommodating a removable rinsing tray in a storage or transport state of the packaging arrangement (1), the rinsing tray can include one or more recesses each of which is configured to receive a rinsing liquid once the packaging arrangement (1) is in a preparation state.

The device recess (2, 20, 21) is preferably configured to receive an oblong medical device (5) in a curved position.

The device recess (2, 20, 21) can be configured to receive at least in part a delivery catheter (5) for a prosthetic heart valve, a cardiovascular occlusion device, an aortic graft or an implantable leadless pacer.

The invention claimed is:

1. A packaging arrangement for a medical device, comprising:
   at least one device recess configured to receive the medical device;
   a loading basin configured to receive a liquid that can manipulate the medical device housed in the at least one device recess or can be connected to the medical device housed in the at least one device recess; and
   a spillway basin, wherein the loading basin is connected to the spillway basin via a spillway passage having a spillway passage inflow and a spillway passage outflow, wherein the spillway passage comprises a downward slope from the spillway passage inflow to the spillway passage outflow configured to promote a liquid flow to the spillway passage outflow, wherein the spillway passage comprises a spillway barrier between the spillway passage inflow and the spillway passage outflow, wherein the liquid flow must overcome the spillway barrier to reach the spillway passage outflow, and wherein the spillway barrier is movable with respect to the spillway passage to allow an adjustment of a height of a top of the spillway barrier.

2. The packaging arrangement according to claim 1, wherein a top of the spillway barrier is higher than the spillway passage inflow and/or spillway passage outflow.

3. The packaging arrangement according to claim 1, wherein a bottom of the spillway basin is located at a height not lower than a height of the loading basin.

4. The packaging arrangement according to claim 1, wherein at least one of the loading basin, the spillway passage and the spillway basin comprises a sidewall having a rim between a top of the sidewall and a bottom of the sidewall, the rim providing an additional volume for a liquid present in a compartment confined by the sidewall.

5. The packaging arrangement according to claim 1, comprising a discharging element in fluid communication with an interior of the loading basin.

6. The packaging arrangement according to claim 5, wherein the discharging element comprises a discharging element inflow oriented to the interior of the loading basin and located at a height that corresponds to at least one of a) a height between an optimum fill level of the loading basin and a top of a sidewall of the loading basin, b) a height between the spillway passage inflow and a top of a sidewall of the loading basin, and c) a height between a top of a spillway barrier and a top of a sidewall of the spillway passage, wherein the spillway barrier is located between the spillway passage inflow and the spillway passage outflow and the liquid flow must overcome the spillway barrier to reach the spillway passage outflow.

7. The packaging arrangement according to claim 5, wherein the discharging element comprises a valve or a removable plugging structure via which a fluid passage within the discharging element can be opened or closed.

8. The packaging arrangement according to claim 5, wherein the discharging element is arranged at a corner of the packaging arrangement.

9. The packaging arrangement according to claim 1, wherein the spillway basin or loading basin is configured to accommodate a removable rinsing tray in a storage or transport state of the packaging arrangement, the removable rinsing tray comprising one or more recesses each configured to receive a rinsing liquid wherein the packaging arrangement is in a preparation state.

10. The packaging arrangement according to claim 1, wherein the at least one device recess is configured to receive an oblong medical device in a curved position.

11. The packaging arrangement according to claim 1, wherein the at least one device recess is configured to receive at least in part a delivery catheter for a prosthetic heart valve, a cardiovascular occlusion device, an aortic graft or an implantable leadless pacer.

12. The packaging arrangement according to claim 5, wherein the discharging element comprises a plug or a valve at a bottom portion of the packaging arrangement.

\* \* \* \* \*